United States Patent [19]
Korsatko-Wabnegg et al.

[11] Patent Number: 5,151,273
[45] Date of Patent: Sep. 29, 1992

[54] DELAYED-RELEASE PHARMACEUTICAL PREPARATION

[75] Inventors: Brigitta Korsatko-Wabnegg; Werner Korsatko, both of Graz; Karlheinz Wegleitner, Linz, all of Austria

[73] Assignee: Lenzing Aktiengesellschaft, Lenzing, Austria

[21] Appl. No.: 676,977

[22] Filed: Mar. 29, 1991

[30] Foreign Application Priority Data

Apr. 4, 1990 [AT] Austria ................................ A803/90

[51] Int. Cl.⁵ .............................................. A61K 9/20
[52] U.S. Cl. .................................... 424/465; 424/443; 424/463; 424/469; 514/800
[58] Field of Search ............... 424/469, 463, 465, 443; 514/264, 800

[56] References Cited

U.S. PATENT DOCUMENTS

| | | | |
|---|---|---|---|
| 4,017,647 | 4/1977 | Ohno | 424/463 |
| 4,367,217 | 1/1983 | Gruber | 424/465 |
| 4,456,628 | 6/1984 | Bauer | 424/463 |
| 4,465,660 | 8/1984 | David | 424/465 |
| 4,581,359 | 4/1986 | Ayres | 514/264 |
| 4,775,660 | 10/1988 | Labrie | 514/800 |
| 4,925,670 | 5/1990 | Schmidt | 424/443 |

*Primary Examiner*—Thurman K. Page
*Assistant Examiner*—William E. Benston
*Attorney, Agent, or Firm*—Herbert Dubno

[57] ABSTRACT

Delayed-release tablets are formed by incorporating hemicellulose and a matrix-forming adjuvant which does not disintegrate in a pharmaceutical dosage form containing the active substance or substances, preferably as a coated tablet or dragee.

6 Claims, 2 Drawing Sheets ature, tablet compositions having up to 20 components
DELAYED-RELEASE PHARMACEUTICAL PREPARATION

FILED OF THE INVENTION

Our present invention relates to a pharmaceutical preparation with a delayed bio-availability, i.e. a delayed-release dosage form of a pharmaceutical composition, generally constituted as a tablet or dragee.

BACKGROUND OF THE INVENTION

It is known in the production of tablets for per oral administration, to provide pharmaceutical dosage forms prior to compressing with adjuvants which, depending upon the characteristics of these adjuvants, provide a certain degree of delayed release of the active substance or substances. The adjuvants applied previously for this purpose have not been fully satisfactory and particularly were lacking with respect to the compression characteristics thereof. Examples of adjuvants of this kind used in the compounding of tablets can be found in *Lehrbuch der pharmazeutischen Technologie*, R Voigt, 5. Aufl., Verlag Chemie, Weinheim (1984), p 178 ff. (Handbook for Pharmaceutical Technology). The adjuvants there described include glidants, binders, fillers, sliding agents, lubricants, disintegrating agents, bumectants, adsorption agents and the like.

It is also known in the production of enterally-dissolvable tablets to subject the tableting compositions to a granulation which can bring about particle flow properties and a bulk density of the powder mixture which is satisfactory for the tableting operation. Indeed these parameters play an important role in the problem-free production of tablets on a mass production basis. The granulation step, is, however, relatively expensive and may require polymers of diverse nature which can function as binders and can effect an aggregation of the powder particles. When one recognizes that in the literature, tablet compositions having up to 20 components are known, it will be readily understood that interactions between active substances and adjuvants (inactive substances) cannot be excluded.

The literature shows countless efforts to develop tableting adjuvants which combine a plurality of such characteristics in one compound so that the number of adjuvants incorporated into a tablet can be reduced It is also desirable to eliminate a granulation step.

Examples of adjuvants which combine a plurality of favorable characteristics include microcrystalline cellulose (Avicel and Heweten) and spray-dried lactose; they are primarily advantageous for slugging and forming tablets without pregranulation.

A hemicellulose, namely Xylan, has already been recognized as a filler and disintegrating agent for tablets. (S.M. Juslin, P. Paronen: Xylan - a possible filler and disintegrant for tablets," J. Pharm. Pharmacol. 1984, 36; 256-257).

According to this publication, hemicellulose is used to produce dosage forms from which the active ingredient is made available immediately upon administration, i.e. within several seconds or at most minutes of administration per os.

In this system, the hemicellulose is used because of its good compression characteristics and because it forms a coherent tablet framework in which the active ingredient to be released is absorbed. The addition of disintegrating agents can be avoided or reduced in this system.

OBJECTS OF THE INVENTION

It is the principal object of the present invention to provide a delayed-release pharmaceutical preparation whereby drawbacks of earlier dosage forms can be avoided.

Another object is to provide an improved tablet or dragee composition and configuration which avoids disadvantages characterizing earlier tableting compositions.

SUMMARY OF THE INVENTION

We have found, most surprisingly in view of the fact that hemicellulose has heretofore been employed as an adjuvant for the preparation of tablets without delayed release of the active substance, that hemicellulose, when incorporated in the pharmaceutical preparation with the active substance or substances and in combination with a nondisintegrating matrix-forming binder, can be used to provide a delayed release of the active ingredients or ingredients over periods of one hour or longer.

More particularly the delayed release enterally administrable pharmaceutical preparation in a dosage form, namely, a tablet or dragee which can be administered per os can comprise at least one pharmaceutically-effective active ingredient capable of enteral administration and a release-delaying composition in which this ingredient is incorporated and which comprises hemicellulose in combination with an enterally nondisintegrating matrix-forming adjuvant.

Hemicellulose has a swellability which progresses at a constant rate and which is therefore directly proportional to time. This characteristic allows, as a consequence, the setting of the disintegration time of the tablet or dragee and a predetermined retardation of the liberation of the active substance from the corresponding tablet or dragee in the sense of a delayed-release effect.

It is an important feature of the invention that the disintegration of the tablet or dragee containing hemicellulose in combination with the binder, i.e. the disintegration of the pressed dosage forms, proceeds independently of the pH value of the liberating medium, i.e. the liquids in the gastrointestinal tract.

Nondisintegrating matrix-forming adjuvants or binders can be combined with the hemicellulose according to the invention because of its reproducible swellability to form pressed bodies with a well-defined delay in release of the active substance in contact with the enteral fluids. The time to release the active substance from such tablets can, depending upon the nature of the matrix-forming adjuvant and the concentration of the hemicellulose incorporated in the composition in accordance with the invention, amount to 1 to 8 hours.

According to a feature of the invention, the tablets which are produced are so-called coated tablets, i.e. tablets having a core and a sheath.

The core can contain the active substance or substances, preferably with a small quantity of hemicellulose which can act as a filter or serve to assist in breaking up the core, while the sheath or coating can consist of the aforementioned composition containing the hemicellulose in combination with the matrix-forming adjuvant.

Depending upon the concentration of hemicellulose in the coating or sheath, access to the active substance in the tablet core is delayed for the desired length of time. The delay in release of the active substance is found to be independent of pH, thereby ensuring that the system will allow a carefully controlled delay release of the active substance. Because it is possible to have the tablet core rapidly disintegrate or act as a sustained release source of the active substance or substances, the tablets or dragees according to the invention can be made with a variety of fields of application.

Coated tablets or dragees of this type have been found to be particularly advantageous for patients with chronic illnesses as well as for patients who cannot be fully attended by physicians and nursing personnel. Especially in such cases, the medicament can be administered in the delayed-release formulation of the invention before the patient goes to sleep. This type of administration is particularly advantageous for medicaments which are effective regardless of the segment of the gastrointestinal tract in which the tablet may be found at the time of the intended release. This type of administration can greatly improve the quality of life of such patients.

According to the invention, the enterally nondisintegrating matrix-forming adjuvant is ethylcellulose, Eudragit RS PM, poly-(L-lactide), poly-(D,L-lactide-coglycolide), or poly-D(—)-3--hydroxybutyrate-cohydroxyvalerate.

The matrix-forming adjuvant is used with respect to the hemicellulose in the following proportion (given as a ratio by weight of hemicellulose to matrix-forming adjuvant):

| | |
|---|---|
| a) Ethylcellulose | (35:65–15:85) |
| b) Eudragit RS PM | (5:95–25:75) |
| c) Poly-(L-lactide) | (35:65–15:85) |
| d) Poly-(D,L-lactide-coglycolide* | (46:60–15:85) |
| e) Poly-D(—)-3-hydroxybutyrate-co-hydroxyvalerate | (5:95–20:80). |

*Note: coglycolide = glycolanhydride

Preferably the hemicellulose has a DP (degree of polymerization) between 10 and 250, preferably 50, a bulk volume of 1.3 to 1.5 ml/g, a particle size of 2 to 50 $\mu$m, and a spherical particle form. It may have an absorption rate (according to Bernard M. Lichstein, Johnson and Johnson: "Demand Wettability and New Method of Measuring Absorbency Characteristics of Gabic", 2.Annual Symp. on Nonwovens Product Development, 1974 Wash. D.C.) of a maximum of 0.3 ml/s.

The hemicellulose recovered from hardwood sulfite cellulose is comprised up to 90% of xylan with a molecular weight of 5300. The remaining 10% is composed of glucan and mannan together. The molecular weight and the composition demonstrate that this product is a strongly degraded hemicellulose. Because of its composition, the water insoluble substance does not form a hydrocolloid like starch, pectin or carboxymethyl cellulose (CMC), but rather has an absorption capacity of 2.8 ml/g which gives rise to a good disintegration effectiveness The spherical form of the particles and the particle size ensure a uniform swelling in an aqueous medium. It is important for the invention that this swelling is pH independent.

The sheath or coating of coated tablets provided with the composition of the invention can have a well-defined time at which the coating will break up and this time can be predetermined and is not influenced by the pH liberation medium, i.e. the liquids in the gastrointestinal tract, by contrast with other systems having delayed release of active substances utilizing stomach secretion-resistant coating. In other words, preprogrammed liberation of the active substance is independent of stomach acidity or intestinal basicity.

The hemicellulose is partly fermented by large intestine bacteria of the human organism, the biological decomposition amounting to between about 40 to 60% of the hemicellulose. The tablet residues residing in the intestine do not give rise to accumulations as can be the case with tablet coatings which are polymer-based and do not decompose with time in the presence of the intestinal secretions.

BRIEF DESCRIPTION OF THE DRAWINGS

The above and other objects, features and advantages of the present invention will become more readily apparent from the following description, reference being made to the accompanying drawing in which.

SPECIFIC DESCRIPTION

Figure 3:
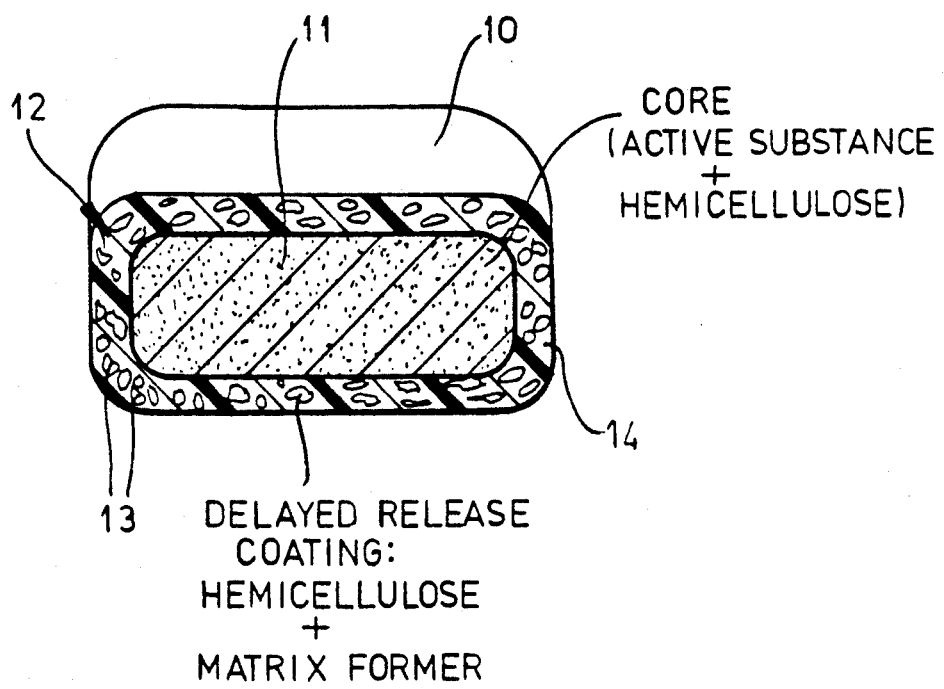
FIG. 3 is a cross-sectional view through a tablet according to the invention.

In FIG. 3 we have shown a tablet 10 which comprises a core 11 containing the active substance or substances in conventional tableting compositions which can, if desired, include hemicellulose. The core 11 containing the active ingredient is surrounded by a coating or sheath 12 containing the hemicellulose 13 in the form of spherical particles in a matrix 14 formed by one of the matrix formers described.

SPECIFIC EXAMPLES

EXAMPLE 1

DETERMINATION OF THE DISINTEGRATION TIME OF HEMICELLULOSE/ /ETHYLCELLULOSE COMPRESSED COMPOSITIONS AS A FUNCTION OF THE MIXTURE RATIO AND PH VALUE.

The components are homogeneously mixed and without pregranulation are compressed by means of an electrohydraulic press at a pressure of 98.1 N per tablet to form tablets. The average weight of a tablet was 100±3 mg. The diameter of the tablets was 7 mm and the height was about 2 mm. The measurements of the disintegration time of the tablets was made in accordance with *Europaischen Arzneibuch*, Bd. III (1981), P. 78 ff. at various pH values. The results are summarized in Table 1. No pH dependency was observed.

TABLE 1

| Mixture Ratio (%) (Hemicellulose/Ethylcellulose) | Disintegration Time (Minutes) | |
|---|---|---|
| | pH 1 | pH 7 |
| 50/50 | 29.1 | 31.7 |
| 40/60 | 41.0 | 41.5 |
| 30/70 | 96.0 | 95.0 |
| 20/80 | 330.0 | 330.0 |
| 10/90 | 440.0 | 420.0 |

EXAMPLE 2

DETERMINATION OF THE DISINTEGRATION TIME OF COMPRESSED COMPOSITIONS OF HEMICELLULOSE AND VARIOUS NON-DISINTEGRATING MATRIX-FORMING ADJUVANTS IN DEPENDENCE UPON PH VALUE.

Hemicellulose is homogeneously mixed with eudragit RS PM, with ethylcellulose with poly-(L-lactide) in a weight ratio of 1:1 with each to form a homogeneous mixture which was compressed into tablets as in Example 1. The results of the disintegration tests (Table 2) shows no pH dependency.

TABLE 2

| | Disintegration Time (Minutes) | | |
|---|---|---|---|
| pH Value | Hemicellulose/ Eudragit RS PM (1:1) | Hemicellulose/ Ethylcellulose (1:1) | Hemicellulose/ Poly-(L-lactide) (1:1) |
| 1 | 5.3 | 29.1 | 24.5 |
| 2 | 5.6 | 29.8 | 24.3 |
| 3 | 5.7 | 30.0 | 24.8 |
| 4 | 5.8 | 30.0 | 26.0 |
| 5 | 6.1 | 30.6 | 26.7 |
| 6 | 6.1 | 30.9 | 27.8 |
| 7 | 6.6 | 31.7 | 31.2 |

EXAMPLE 3

DETERMINATION OF THE DISINTEGRATION TIME FOR COMPACTS OF HEMICELLULOSE/EUDRAGIT RS PM IN DEPENDENCY UPON MIXING RATIO AND PH VALUE

Various weight ratios of hemicellulose and eudragit RS PM in the range of 90:10 and 10:90 are formed into tablets as in Example 1 and subjected to disintegration tests. The results (Table 3) show no pH dependency.

TABLE 3

| Mixture Ratio (%) (Hemicellulose/Eudragit RS PM) | Disintegration Time (Minutes) | | |
|---|---|---|---|
| | pH 1 | pH 4 | pH 7 |
| 90/10 | 9.1 | 11.4 | 12.0 |
| 80/20 | 8.1 | 10.1 | 10.6 |
| 70/30 | 5.9 | 7.7 | 6.9 |
| 60/40 | 5.2 | 6.3 | 6.5 |
| 50/50 | 5.3 | 5.6 | 6.3 |
| 40/60 | 2.2 | 2.7 | 2.6 |
| 30/70 | 1.0 | 1.0 | 1.0 |
| 20/80 | 2.5 | 3.0 | 3.0 |
| 10/90 | 106.6 | 113.2 | 145.0 |

EXAMPLE 4

PRODUCTION OF COATED TABLETS WITH RAPIDLY DISINTEGRATING CORES

| | Tablet core: |
|---|---|
| A) | 5 mg 7-Hydroxyethyltheophylline |
| | 6 mg Ethylcellulose |
| | 14 mg Hemicellulose |
| B) | 5 mg 7-Hydroxyethyltheophylline |
| | 20 mg Granulatum simplex (Lehrbuch der pharmazeutischen Technologie, R. Voigt, P. 178) |
| C) | 5 mg 7-Hydroxyethyltheophylline |
| | 19 mg Granulatum simplex |
| | 1 mg Hemicullulose |

The compounds are homogeneously mixed and compressed at a pressure of 49.05 N/Tablet to tablets of an average weight of 25±0.3 mg, a diameter of 4 mm and a height of 1.2 mm, to form the cores.

| | Tablet Sheath |
|---|---|
| I) | 157.5 mg Ethylcellulose |
| | 67.5 mg Hemicellulose |
| II) | 180.0 mg Ethylcellulose |
| | 45.0 mg Hemicellulose |

For the production of the coated tablets, the tablet cores A, B and C are incorporated in sheaths of the compositions I and II by compressing. The dimensions of the coated tablets were:

| Weight: | 250 mg ± 1.5 mg |
|---|---|
| Diameter: | 9.0 mm |
| Height: | 4.5 mm. |

The delayed-release effect was measured by the "half-change" method (R. Voigt, Lehrbuch der pharmazeutischen Technologie, P. 627) by spectral photometric determination of the liberated 7-hydroxy-ethyltheophylline at 273 nm. The results are given in Table 4 for the coated tablets with the coating I and in Table 5 for the tablet coating II.

TABLE 4

| | Release of Active Substance from Tablet Core (%) | | |
|---|---|---|---|
| Hours | A | B | C |
| 1 | — | — | — |
| 2 | 28.9 | 20.0 | 9.6 |
| 3 | 98.3 | 91.7 | 81.7 |
| 4 | 100.0 | 94.5 | 89.1 |
| 5 | 100.0 | 100.0 | 100.0 |

Retarding of onset of activity: 2 hours.

TABLE 5

| | Release of Active Substance from Tablet Core (%) | | |
|---|---|---|---|
| Hours | A | B | C |
| 6 | — | — | — |
| 7 | 70.3 | — | — |
| 8 | 100.0 | 64.5 | 58.8 |
| 9 | 100.0 | 95.3 | 92.0 |
| 10 | 100.0 | 100.0 | 100.0 |

Retardation of activity: 7 to 7.5 hours.

EXAMPLE 5

PRODUCTION OF COATED TABLETS WITH RETARDING TABLET CORE

| Tablet core: | 5 mg 7-Hydroxyethyltheophylline |
|---|---|
| | 20 mg Ethylcellulose |

The table core is made as in Example 4.

| Tablet sheath: | 157.5 mg Ethylcellulose |
|---|---|
| | 67.5 mg Hemicellulose |

Figure 1:
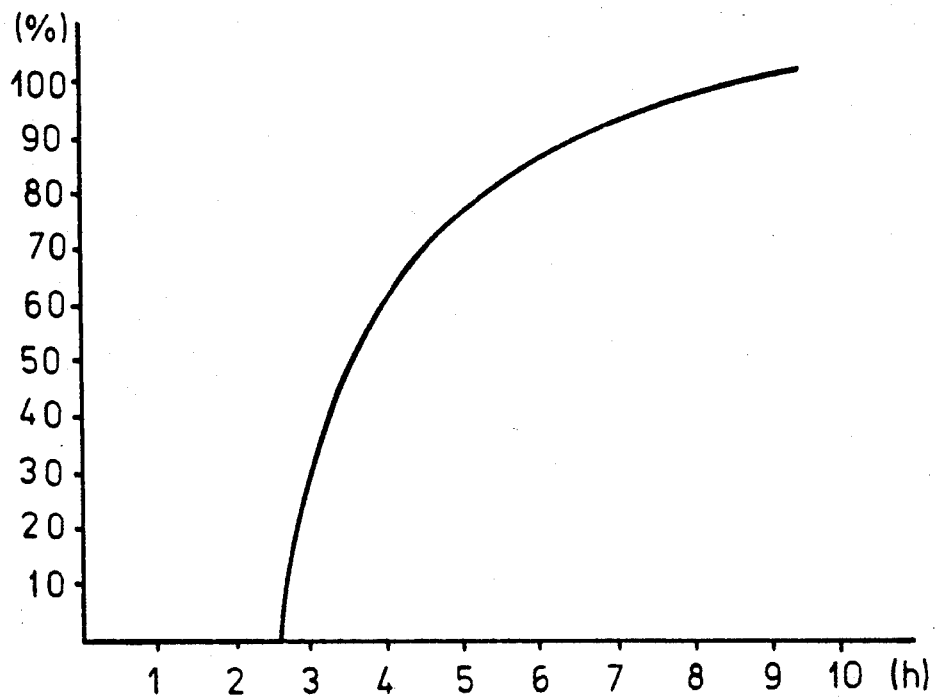
FIGS. 1 and 2 are diagrams illustrating the invention.

The production and testing of the coated tablet is effected as in Example 4. The results are shown in FIG. 1 and Table 6.

TABLE 6

| Hours | Release of Active Substance from Tablet Core (%) |
|---|---|
| 2 | — |
| 3 | 30.9 |

TABLE 6-continued

| Hours | Release of Active Substance from Tablet Core (%) |
|---|---|
| 4 | 77.4 |
| 6 | 88.9 |
| 7 | 92.8 |
| 8 | 96.1 |
| 9 | 100.0 |

Delay in onset of activity: 2.5 hours.

EXAMPLE 6

Figure 2:
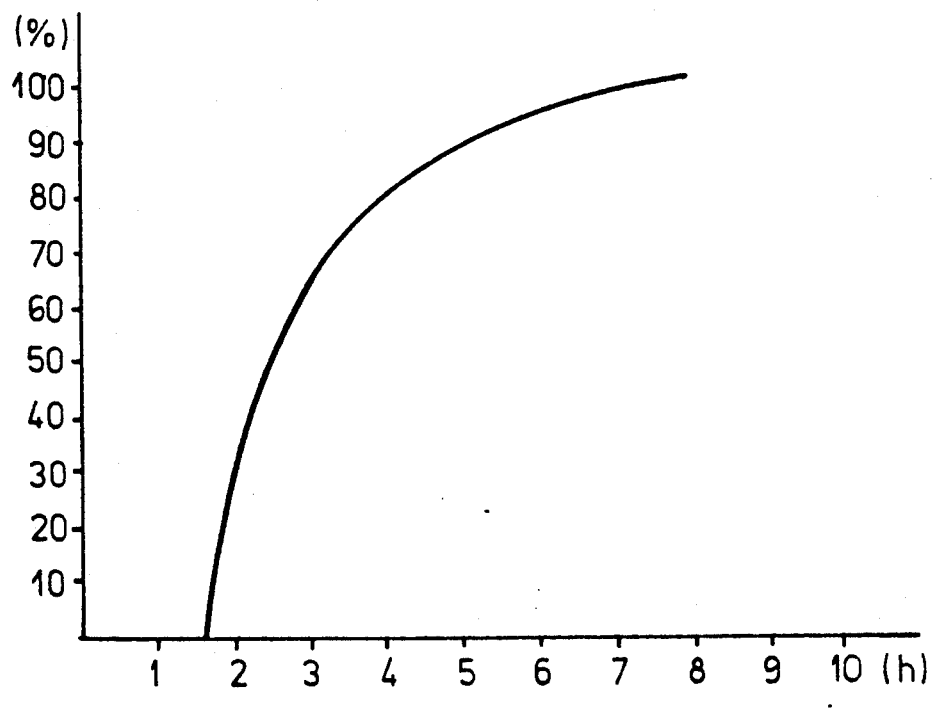

Example 5 was followed except that poly-(L-lactide) was used as the matrix in place of the ethylcellulose. The results are illustrated in Table 7 and FIG. 2.

TABLE 7

| Hours | Release of Active Substance from Tablet Core (%) |
|---|---|
| 1 | — |
| 2 | 38.8 |
| 3 | 68.2 |
| 4 | 80.4 |
| 5 | 89.7 |
| 6 | 94.1 |
| 7 | 97.8 |
| 8 | 100.0 |

Delay in onset of activity: 1.5 hours.

We claim:

1. A delayed-release enterally active pharmaceutical preparation in a dosage form, comprising a core and a covering, at least one pharmaceutically effective active substance in said core capable of enteral administration and a release-delaying composition forming said covering and which comprises hemicellulose in combination with a non-disintegrating matrix-forming adjuvant, said non-disintegrating matrix-forming adjuvant being poly-D(−)-3-hydroxybutyrate-cohydroxyvalerate, the weight ratio of the hemicellulose to the poly-D(−)-3-hydrosybutyrate-cohydroxyvalerate in said composition being 5:95 to 20:80.

2. The delayed-release enterally active pharmaceutical preparation in a dosage form defined in claim 1 wherein said dosage form is a table.

3. The delayed-release enterally pharmaceutical preparation in a dosage form defined in claim 1 wherein said dosage form is a dragee.

4. The delayed-release enterally active pharmaceutical preparation in a dosage form defined in claim 1 wherein said hemicellulose has a DP between 10 and 250, a bulk volume of 1.3 to 1.5 ml/g, a particle size of 2 to 50 μm, a generally spherical particle configuration and an absorption rate according to B.H. Lichstein of a maximum of 0.3 ml/s.

5. The delayed-release enterally active pharmaceutical preparation in a dosage form defined in claim 4 wherein said hemicellulose has a DP of about 50 and a particle size of 10 to 20 μm.

6. The delayed-release enterally administrable pharmaceutical preparation in a dosage form defined in claim 5 wherein said pharmaceutically effective active substance is 7-hydroxyethyltheophylline.

* * * * *